US006458147B1

(12) United States Patent
Cruise et al.

(10) Patent No.: US 6,458,147 B1
(45) Date of Patent: *Oct. 1, 2002

(54) COMPOSITIONS, SYSTEMS, AND METHODS FOR ARRESTING OR CONTROLLING BLEEDING OR FLUID LEAKAGE IN BODY TISSUE

(75) Inventors: Gregory M Cruise, Fremont; Olexander Hnojewyj, Saratoga, both of CA (US)

(73) Assignee: NeoMend, Inc., Sunnyvale, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/283,535
(22) Filed: Apr. 1, 1999

Related U.S. Application Data

(63) Continuation-in-part of application No. 09/188,033, filed on Nov. 6, 1998.

(51) Int. Cl.$^7$ .............................................. A61B 17/04
(52) U.S. Cl. ....................................................... 606/214
(58) Field of Search ................................ 606/213–215; 424/448, 443; 128/898

(56) References Cited

U.S. PATENT DOCUMENTS

| 4,101,380 A | 7/1978 | Rubinstein et al. |
| 4,161,948 A | 7/1979 | Bichon |
| 4,464,468 A | 8/1984 | Avrameas et al. |
| 4,839,345 A | 6/1989 | Doi et al. |
| 5,051,406 A | 9/1991 | Satoh |
| 5,129,882 A | 7/1992 | Weldon et al. |
| 5,207,670 A | 5/1993 | Sinofsky |
| 5,252,714 A | 10/1993 | Harris et al. |
| 5,318,524 A | * 6/1994 | Morse et al. .................. 604/82 |
| 5,383,896 A | 1/1995 | Gershony et al. |
| 5,403,278 A | 4/1995 | Ernst et al. |
| 5,410,016 A | 4/1995 | Hubbell et al. |
| 5,419,765 A | 5/1995 | Weldon et al. |
| 5,514,379 A | 5/1996 | Weissleder et al. |
| 5,520,885 A | 5/1996 | Coelho et al. |

(List continued on next page.)

FOREIGN PATENT DOCUMENTS

| WO | WO 96/11671 | 4/1996 |
| WO | WO 97/22371 | 6/1997 |
| WO | WO 99/07417 | 2/1999 |
| WO | WO 99/14259 | 3/1999 |
| WO | WO 99/45964 | 9/1999 |
| WO | WO 00/09087 | 2/2000 |
| WO | WO 00/09199 | 2/2000 |
| WO | WO 00/33764 | 6/2000 |
| WO | WO 00/62827 | 10/2000 |

OTHER PUBLICATIONS

West JL et al Proteolytically Degradable Hydrogels Apr. 30–May 4, 1997 23$^{rd}$ Anr the Society for Biomaterials New Orleans Louisiana.

Primary Examiner—Olik Chaudhuri
Assistant Examiner—Vikki Hoa Trinh
(74) Attorney, Agent, or Firm—Ryan Kromholz & Manion, S.C.

(57) ABSTRACT

A biocompatible and biodegradable hydrogel compound, which is free of a hemostatic agent, is applied to arrest the flow of blood or fluid from body tissue. The compound preferably includes a protein comprising recombinant or natural serum albumin, which is mixed with a polymer that comprises poly(ethylene) glycol (PEG), and, most preferably, a multi-armed PEG polymer.

75 Claims, 10 Drawing Sheets

U.S. PATENT DOCUMENTS

| | | | |
|---|---|---|---|
| 5,529,577 | A | 6/1996 | Hammerslag |
| 5,567,435 | A | 10/1996 | Hubbell et al. |
| 5,583,114 | A | 12/1996 | Barrows et al. |
| 5,601,602 | A | 2/1997 | Fowler |
| 5,626,601 | A | 5/1997 | Gershony et al. |
| 5,626,863 | A | 5/1997 | Hubbell et al. |
| 5,653,730 | A | 8/1997 | Hammerslag |
| 5,672,662 | A | 9/1997 | Harris et al. |
| 5,676,689 | A | 10/1997 | Kensey et al. |
| 5,725,498 | A | 3/1998 | Janzen et al. |
| 5,733,563 | A | 3/1998 | Fortier |
| 5,739,208 | A | 4/1998 | Harris |
| 5,759,194 | A | 6/1998 | Hammerslag |
| 5,782,860 | A | 7/1998 | Epstein et al. |
| 5,791,352 | A | 8/1998 | Reich et al. |
| 5,824,015 | A * | 10/1998 | Sawyer ................. 606/214 |
| 5,843,124 | A | 12/1998 | Hammerslag |
| 5,844,016 | A | 12/1998 | Sawhney et al. |
| 5,858,746 | A * | 1/1999 | Hubbell et al. ............ 435/177 |
| 5,874,500 | A | 2/1999 | Rhee et al. |
| 5,900,245 | A | 5/1999 | Sawhney et al. |
| 5,900,461 | A | 5/1999 | Harris |
| 5,922,009 | A | 7/1999 | Epstein et al. |
| 5,932,462 | A | 8/1999 | Harris et al. |
| 5,935,147 | A | 8/1999 | Kensey et al. |
| 5,936,035 | A | 8/1999 | Rhee et al. |
| 5,942,209 | A | 8/1999 | Leavitt et al. |
| 5,951,583 | A | 9/1999 | Jensen et al. |
| 5,951,589 | A | 9/1999 | Epstein et al. |
| 5,986,043 | A | 11/1999 | Hubbell et al. |
| 5,990,237 | A | 11/1999 | Bentley et al. |
| 6,007,613 | A | 12/1999 | Izoret |
| 6,022,361 | A | 2/2000 | Epstein et al. |
| 6,051,248 | A | 4/2000 | Sawhney et al. |
| 6,060,582 | A | 5/2000 | Hubbell et al. |
| 6,083,524 | A | 7/2000 | Sawhney et al. |
| 6,152,943 | A | 11/2000 | Sawhney |
| 6,162,241 | A | 12/2000 | Coury et al. |
| 6,165,201 | A | 12/2000 | Sawhney et al. |
| 6,177,095 | B1 | 1/2001 | Sawhney et al. |
| 6,179,862 | B1 | 1/2001 | Sawhney |

* cited by examiner

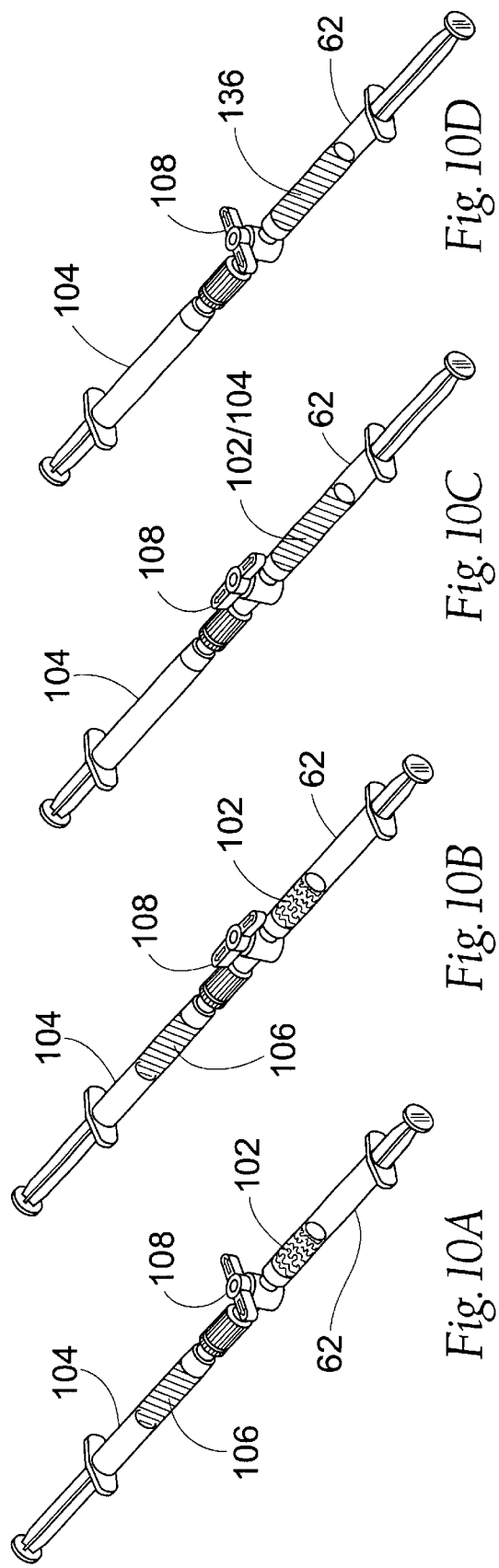

COMPOSITIONS, SYSTEMS, AND METHODS FOR ARRESTING OR CONTROLLING BLEEDING OR FLUID LEAKAGE IN BODY TISSUE

RELATED APPLICATION

This application is a continuation-in-part of U.S. patent application Ser. No. 09/188,083, filed Nov. 6, 1998 and entitled "Compositions, Systems, and Methods for Creating in Situ, Chemically Cross-linked, Mechanical Barriers."

FIELD OF THE INVENTION

The invention generally relates systems and methods for arresting or controlling the bleeding or leakage of fluid in body tissues, e.g., diffuse organ bleeding, lung punctures, anastomotic leakage, and the like.

BACKGROUND OF THE INVENTION

Hemostatic barriers are routinely called upon to control bleeding. The bleeding may be caused by trauma, e.g. splenic, kidney, and liver lacerations, or may be caused during surgery, e.g. tumor removal or bone bleeding.

Bleeding is conventionally controlled by the application of solid sheets of material, e.g. gauze, Gelfoam™ material, or Surgicel™ material. These materials can be soaked with a hemostatic agent, such as thrombin or epinephrine, or sprayable formulations such as fibrin glue.

Conventional treatment modalities require the use of these hemostatic agents in conjunction with pressure to achieve hemostasis. The various hemostatic agents can include coagulation factors (e.g. thrombin), platelet activators (e.g. collagen), vasoconstrictors (epinephrine), or fibrinolytic inhibitors.

In some instances, conventional treatments achieve hemostasis in a clinically acceptable time. Still, there are a number of drawbacks.

For example, many treatment modalities consist of bovine collagen and bovine thrombin to cause the desired clotting action. These products have the potential for the transmission to humans of bovine spongiform encephalopathy (also called "Mad Cow Disease"). Regardless, the bovine thrombin marketed today is relatively impure, and these impurities can lead to complications in certain patient populations. Furthermore, fibrin glue, generally composed of purified fibrinogen and thrombin from pooled human blood, has safety and efficacy concerns as well. Additionally, many products do not achieve hemostasis in a clinically acceptable period, particularly in cases of brisk bleeding.

In addition to hemostatic agents, surgical sealants are also commonly used to control bleeding or fluid leakage along anastomoses formed by suture or staple lines, e.g., between blood vessels, bowel, or lung tissue. In cases of blood leakage, fibrin glue can be utilized to seal an anastomosis. Still, fibrin glue's lack of adhesion to moist tissue, safety concerns, and cost precludes its widespread use as a surgical sealant for blood vessel anastomoses.

Conventional hemostatic agents and surgical sealants for blood vessel anastomoses achieve hemostasis using the application of pressure and by activating the coagulation pathway of the blood. Yet, many of the surgeries where hemostatic barriers and surgical sealants are required also require the administration of anti-coagulation therapies, such as heparin. The hemostatic barrier or surgical sealant, which is promoting coagulation, is hindered by the effect of the heparin, which is preventing coagulation.

Despite conventional treatment modalities for hemostatic barriers and surgical sealants, there is a need for a biomaterial that safely, quickly, and reliably arrests or controls fluid leakage in body tissues through the application of pressure and without interaction with the patient's coagulation pathways.

SUMMARY OF THE INVENTION

The invention provides compositions, instruments, systems, and methods, which arrest or control bleeding or leakage of fluid in body tissue.

According to one aspect of the invention, a biocompatible and biodegradable material is provided which comprises a hydrogel compound free of a hemostatic agent and which, when applied by instruments, systems, and methods that embody the invention, arrests the flow of blood or fluid from body tissue.

According to another aspect of the invention, a biocompatible and biodegradable material is provided which comprises a hydrogel compound free of a hemostatic agent and which, when applied by instruments, systems, and methods that embody the invention, arrests organ diffuse bleeding.

According to another aspect of the invention, a biocompatible and biodegradable material is provided which comprises a protein solution and a polymer solution including a derivative of a hydrophilic polymer with a functionality of at least three, which, when mixed by instruments, systems, and methods that embody the invention, form a mechanical non-liquid covering structure that arrests the flow of blood or seals tissue.

Features and advantages of the inventions are set forth in the following Description and Drawings, as well as in the appended claims.

BRIEF DESCRIPTION OF THE DRAWINGS

FIGS. 10A to 10D are perspective views showing the manipulation of syringes contained in the kit shown in FIG. 6A, to create a liquid PEG solution for use with the system shown in FIG. 1.

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

DETAILED DESCRIPTION OF THE PREFERRED EMBODIMENTS

Figure 1:
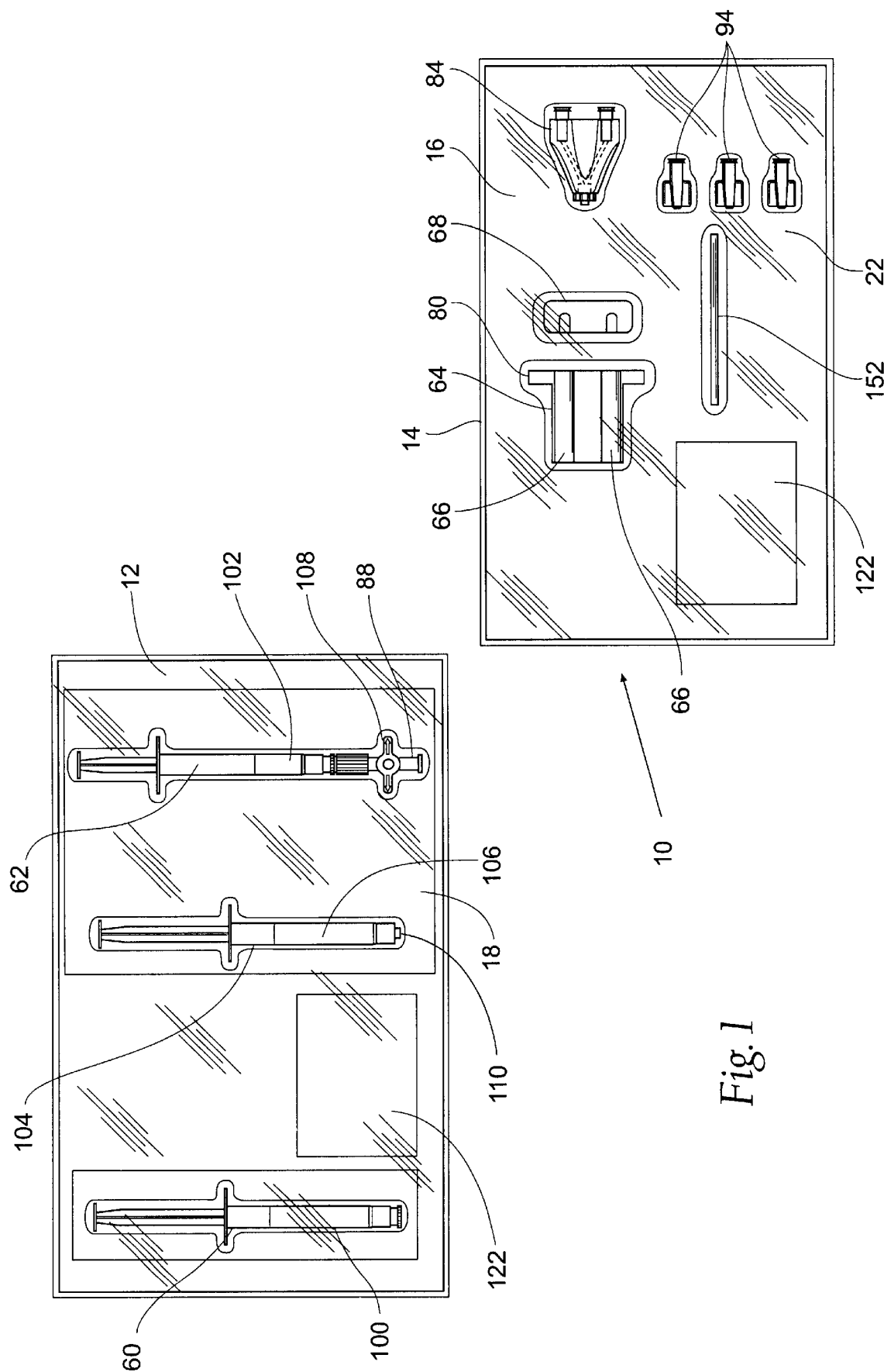
FIG. 1 is a plan view of a system for arresting or controlling bleeding or leakage of fluid in body tissue, showing the components of the system prepackaged in sterile kits.

FIG. 1 shows a system 10 of functional instruments for arresting or controlling the loss of blood or other fluids in body tissue.

Figure 2:
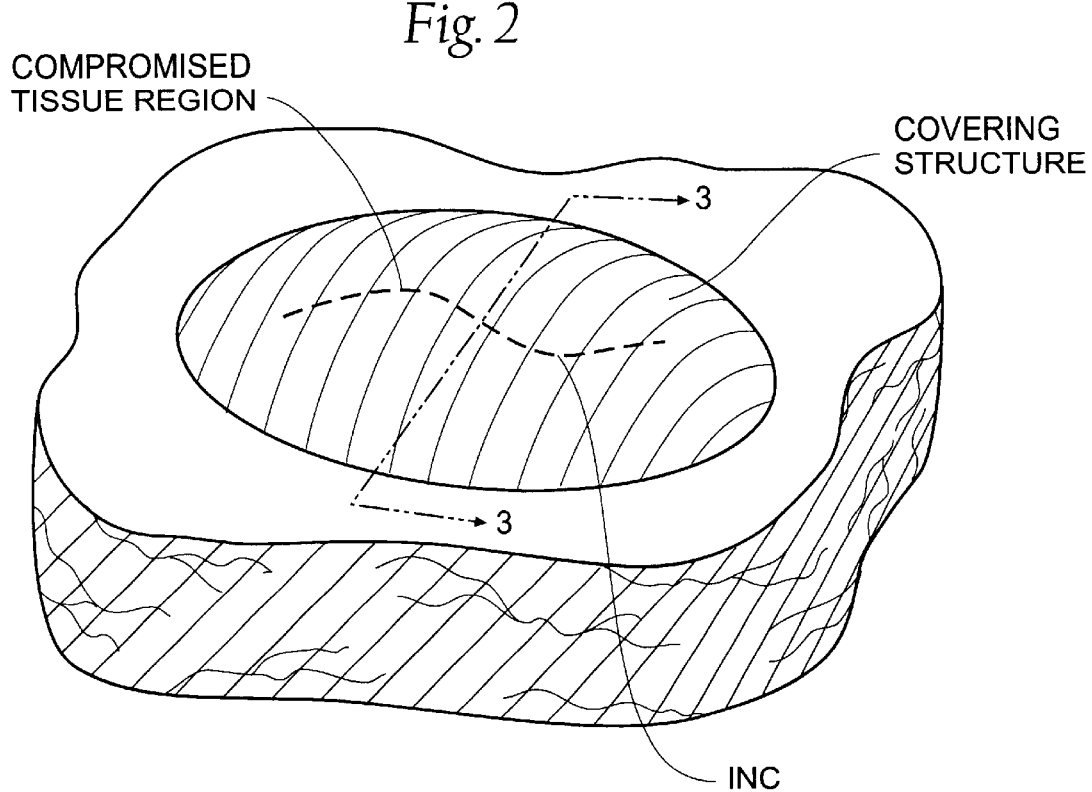
FIG. 2 is a diagrammatic view of a compromised tissue region, upon which a covering structure that embodies the features of the invention has been dispersed to arrest or control bleeding.
Figure 3:
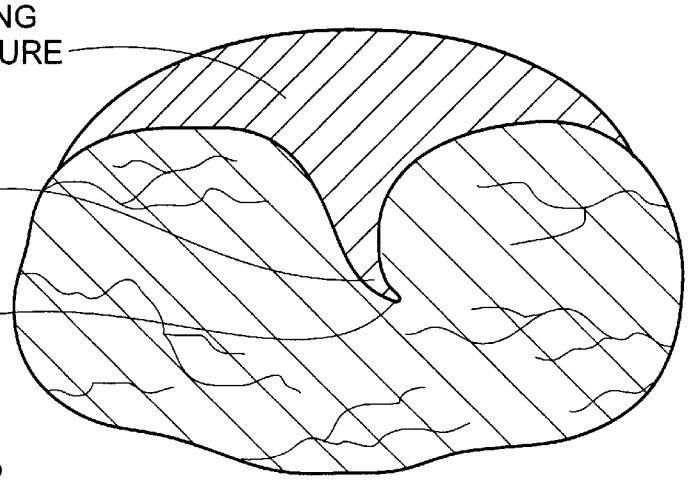
FIG. 3 is a side view of the covering structure shown in FIG. 2, taken generally along line 3—3 in FIG. 2.

During use, the instruments of the system 10 are brought to a compromised tissue region (shown as an incision INC in FIGS. 2 and 3), where bleeding or loss of another body fluid is occurring, e.g., due to diffuse bleeding or anastomosis. The parts of the system 10 are manipulated by a physician or medical support personnel to create a liquid material, which is immediately dispersed as a spray directly onto the surface of the compromised tissue region. The liquid material transforms as it is being dispersed as a result of cross-linking into an in situ-formed non-liquid covering structure. The covering structure intimately adheres and conforms to the surface the compromised tissue region, as FIG. 3 best shows.

Due to the physical characteristics of the covering structure and the speed at which it forms in situ, the presence of the covering structure mechanically arrests or blocks further blood or fluid loss from the compromised tissue region, without need for a hemostatic agent. The covering structure exists long enough to prevent blood or fluid leakage while the compromised tissue region heals by natural processes. The covering structure is, over time, degraded by hydrolysis by in the host body and cleared by the kidneys from the blood stream and removed in the urine.

In the illustrated embodiment (see FIG. 1), the system 10 is consolidated in two functional kits 12 and 14.

The kit 12 houses the component assembly 18, which contains the formative components from which the covering structure is created. The kit 12 holds the components in an unmixed condition until the instant of use.

The kit 14 contains a dispersing assembly 16. The dispersing assembly 16 brings the components in the assembly 18, while in liquid form, into intimate mixing contact. At the same time, the assembly 16 disperses the liquid mixture onto the surface of the compromised tissue region, to ultimately form the in situ covering structure.

I. The Covering Structure

The covering structure comprises a material that is chemically cross-linked, to form a non-liquid mechanical matrix or barrier.

In a preferred embodiment, the material of the covering structure is a protein/polymer composite hydrogel. The material is most preferably formed from the mixture of a protein solution and a solution of an electrophilic derivative of a hydrophilic polymer with a functionality of at least three. The material is nontoxic, biodegradable, and possesses mechanical properties such as cohesive strength, adhesive strength, and elasticity sufficient to block or arrest diffuse organ bleeding, or to block or arrest seepage as a result of anastomosis, or to seal lung punctures.

The material also permits the rate of cross-linking and gelation to be controlled through buffer selection and concentration. The rate of degradation after cross-linking can be controlled through the selection of a degradation control region.

A. Material Components

In the illustrated embodiment (see FIG. 1), the component assembly 18 includes first and second dispensing syringes 60 and 62, in which the formative components of the covering structure are stored prior to use.

(i) Natural Plasma-Based Protein

The first dispensing syringe 60 contains a concentration of buffered protein solution 100. The protein solution is supplemented with the appropriate buffers, sterile filtered, aseptically filled into the syringe 60, and the syringe 60 is capped for storage prior to use.

Suitable proteins for incorporation into material include non-immunogenic, hydrophilic proteins. Examples include solutions of albumin, gelatin, antibodies, serum proteins, serum fractions, and serum. Also, water soluble derivatives of hydrophobic proteins can also be used. Examples include collagen, fibrinogen, elastin, chitosan, and hyaluronic acid. The protein can be produced from naturally occurring source or it may be recombinantly produced.

The preferred protein solution is 25% human serum albumin, USP. Human serum albumin is preferred due to its biocompatibility and its ready availability.

Buffer selection and concentration maintains the pH of the reactive mixture. Buffers that are well tolerated physiologically can be used. Examples include carbonate and phosphate buffer systems. Care should be taken to select buffers that do not participate in or interfere with the cross-linking reaction. The preferred range of buffer concentration is from about 0.03 M to about 0.4 M, and the preferred range of pH is from about 7.0 to about 10.0. A preferred buffer system for the covering structure is carbonate buffer at a concentration of 0.315 M at a pH value of about 9 to about 10. As will be described later, there is a relationship between pH and the time for cross-linking (also called "gelation").

(ii) Electrophilic Water Soluble Polymer

In the illustrated embodiment (still referring principally to FIG. 1), the second dispensing syringe 62 contains an inert, electrophilic, water soluble polymer 102. The polymer cross-links the protein to form an inert, three dimensional mechanical network or matrix. The matrix forms the mechanical covering structure. The covering structure adheres and conforms to the surface of the tissue region on which it is dispensed. The covering structure is, over time, resorbed.

The polymer 102 comprises a hydrophilic, biocompatible polymer, which is electrophilically derivatized with a functionality of at least three. A number of polymers could be utilized, including poly(ethylene glycol), poly(ethylene oxide), poly(vinyl alcohol), poly(vinylpyrrolidone), poly(ethyloxazoline), and poly(ethylene glycol)-co-poly(propylene glycol) block copolymers. The polymer portion is not restricted to synthetic polymers as polysaccharides, carbohydrates, and proteins could also be electrophilically derivatized.

Preferably, the polymer 102 is comprised of poly(ethylene glycol) (PEG) with a molecular weight between 1,000 and 30,000 g/jmole, more preferably between 2,000 and 15,000 g/mole, and most preferably between 10,000 and 15,000 g/mole. PEG has been demonstrated to be biocompatible and non-toxic in a variety of physiological applications.

The preferred polymer can be generally expressed as compounds of the formula:

PEG-(DCR-CG)$_n$ where:

DCR is a degradation control region.

CG in a cross-linking group.

n≦3

While the preferred polymer is a multi-armed structure, a linear polymer with a functionality of at least three can also be used. The desired functionality of the PEG polymer for forming the covering structure can be expressed in terms of (i) how quickly the polymer cross-links the protein and transforms to a nonfluent gel state (i.e., the mechanical material) (a preferred gelation time is under three seconds), and (ii) the mechanical properties of the covering structure after gelation in terms of its liquid sealing characteristics, physical strength, resistance to fragmentation (i.e., brittleness), and bioresorption. The optimization of both attributes (i) and (ii) is desirable.

The inventors have discovered that the utility of a given PEG polymer significantly increases when the functionality is increased to be greater than or equal to three. The observed incremental increase in functionality occurs when the functionality is increased from two to three, and again when the functionality is increased from three to four. Further incremental increases are minimal when the functionality exceeds about four.

The use of PEG polymers with functionality of greater than three provides a surprising advantage. When cross-linked with higher functionality PEG polymers, the concentration of albumin can be reduced to 25% and below. Past uses of difunctional PEG polymers require concentrations of albumin well above 25%, e.g. 35% to 45%. Use of lower concentrations of albumin results in superior sealing properties with reduced brittleness, facilitating reentry through the nonfluid material, without fragmentation. Additionally, 25% human serum albumin, USP is commercially available from several sources, however higher concentrations of USP albumin are not commercially available. By using commercially available materials, the dialysis and ultrafiltration of the albumin solution, as disclosed in the prior art, is eliminated, significantly reducing the cost and complexity of the preparation of the albumin solution.

In the illustrated embodiment, the polymer 102 is initially packaged prior to use in the second dispensing syringe 62 in an inert atmosphere (e.g., argon) in a stable, powder form. In this arrangement, the component assembly 18 includes a third syringe 104, which contains sterile water 106 for dissolution of the powder polymer 102 just before mixing with the albumin component 100.

In facilitating mixing, a stopcock valve 108 is secured to the luer fitting 88 at the dispensing end of the second dispensing syringe 62. The dispensing end 110 of the water syringe 104 couples to the stopcock valve 108, so that the water 106 can be mixed with the polymer 102 in the dispensing syringe 62 prior to use.

(a) Selection of the Degradation Control Region DCR

The rate of degradation is controlled by the selection of chemical moiety in the degradatioh control region DCG. If degradation is desired, a hydrolytically or enzymatically degradable moiety can be selected, Examples of hydrolytically degradable moieties include saturated di-acids, unsaturated di-acids, poly(glycolic acid), poly(DL-lactic acid), poly(L-lactic acid), poly(ε-caprolactone), poly(δ-valerolactone), poly(γ-butyrolactone), poly(amino acids), poly(anhydrides), poly(orthoesters), poly (orthocarbonates), and poly(phosphoesters).

Examples of enzymatically degradable regions include Leu-Glyc-Pro-Ala (collagenase sensitive linkage) and Gly-Pro-Lys (plasmin sensitive linkage).

The preferred degradable control regions for degradable materials are ester containing linkages, as are present when succinic acid or glutaric acid are coupled to a PEG molecule. The preferred degradable control regions for nondegradable materials are ether containing linkages. The material can also be created without the introduction of a degradation control region.

(b) Selection of the Cross-Linking Group CG

The cross-linking group is responsible for the cross-linking of the albumin, as well as the binding to the tissue substrate. The cross-linking group can be selected to selectively react with sulfhydryl groups, selectively react with amines, or can be selected to react with sulfhydryl, primary amino, and secondary amino groups. Cross-linking groups that react selectively with sulfhydryl groups include vinyl sulfone, N-ethyl maleimide, iodoacetamide, and orthopyridyl disulfide. Cross-linking groups specific to amines include aldehydes. Non-selective electrophilic cross-linking groups include active esters, epoxides, carbonylimidazole, nitrophenyl carbonates, tresylate, mesylate, tosylate, and isocyanate. The preferred cross-linking group is an active ester, specifically an ester of N-hydroxysuccinimide.

To minimize the liberation of heat during the cross-linking reaction, the concentration of the cross-linking groups is preferably kept less than 5% of the total mass of the reactive solution, and more preferably about 1% or less. The low concentration of the cross-linking group is also beneficial so that the amount of the leaving group is also minimized. In a preferred embodiment, the cross-linking group portion comprising a N-hydroxysuccinimide ester has demonstrated ability to participate in the cross-linking reaction with albumin without presenting the risk of local or systemic immune responses in humans.

(c) Preferred Multiple Arm PEG Polymer

In a preferred embodiment, the polymer is comprised of a 4-arm PEG with a molecular weight of about 10,000 g/mole, the degradation control region is comprised of glutaric acid, and the cross-linking group is comprised of a N-hydroxysuccinimide ester. Thus, a preferred polymer is poly(ethylene glycol) tetra-succinimidyl glutarate, which is available from Shearwater Polymers, Huntsville, Ala. The preferred polymer will, in shorthand, be called 4-PEG-SG. The polymer is dissolved in water prior to use. Preferred concentrations of the polymer are from 5% to 35% w/w in water.

The solution of 4-PEG-SG mixes with 25% serum albumin to form a liquid solution that quickly cross-links to form a non-liquid, three dimensional network for the covering structure. With these material formulations, it is possible to intimately mix the water soluble polymer with the albumin protein using, e.g., atomization, or static mixing, or in-line channel mixing.

As will be demonstrated later, the rate of reaction can be controlled by the pH of the reactive solution. An increase in temperature is not observed during formation of the covering structure network, due to the low concentration of reactive groups, which account for only about 1% of the total mass. In a typical clinical application, about 50 mg of a non-toxic leaving group is produced during the cross-linking reaction, which is a further desired result.

The resulting nonfluent material created by mixing 25% albumin and 4-PEG-SG is approximately 80% water, 13% albumin, and 7% PEG. The material is well tolerated by the body, without invoking a severe foreign body response. Over a controlled period of time, the material is degraded via hydrolysis. Histological studies have shown a foreign body response consistent with a biodegradable material, such as VICRYL™ sutures. As the material is degraded, the tissue returns to a quiescent state. The molecules of the degraded material are cleared from the bloodstream by the kidneys and eliminated from the body in the urine. In a preferred embodiment of the invention, the material loses its physical strength during the first twenty days, and total resorption occurs in about 4 weeks.

The following Examples demonstrate the superior features of the material of the invention.

EXAMPLE 1

Preparation of Cross-Linked Networks

Cross-linked covering structure networks were formed by the mixture of an 4-PEG-SG and albumin. A solution of 4-PEG-SG was prepared by dissolving 0.40 g in 2.0 mL of water. The albumin solution consisted 25% human serum alburmin, USP (Plasbumin-25, Bayer Corporation), as received.

Dispensing syringes containing 2.0 mL of the polymer solution and 2.0 mL of albumin solution were connected to the joiner 84, to which a spray head was coupled. The solutions were sprayed into a polystyrene weigh boat. A cross-linked covering structure network formed at room temperature in about 90 seconds.

EXAMPLE 2

Control of the Rate of Gelation

The rate of formation of the cross-linked covering structure network of 4-PEG-SG and albumin (i.e., gelation) can be controlled by the pH of the reactive solution. To increase the rate of cross-linking, the pH of the solution is increased, and conversely, to decrease the rate of cross-linking, the pH of the solution is decreased. The pH of the solution is controlled by both the buffer strength and buffer pH.

Table 1 shows the effect of buffer strength on the rate of gelation of 17% w/w 4-PEG-SG in water for injection and 25% human serum albumin, USP at room temperature. The rate of gelation can also be controlled by adjusting the pH of the buffer at a constant buffer concentration. The buffer was placed in the solution of albumin. The gelation time is the amount of time required for the formulation to transform from the liquid state to the cross-linked solid state.

TABLE 1

Effect of Buffer strength and Buffer pH on Gel Formation

| Buffer Concentration | Buffer pH | Gelation Time |
| --- | --- | --- |
| 300 mM | 9 | <1 sec |
| 200 mM | 9 | 5 sec |
| 100 mM | 9 | 10 sec |
| 50 mM | 9 | 20 sec |
| 0 mM | 7 | 90 sec |

II. The Dispersing Assembly

Figure 4:
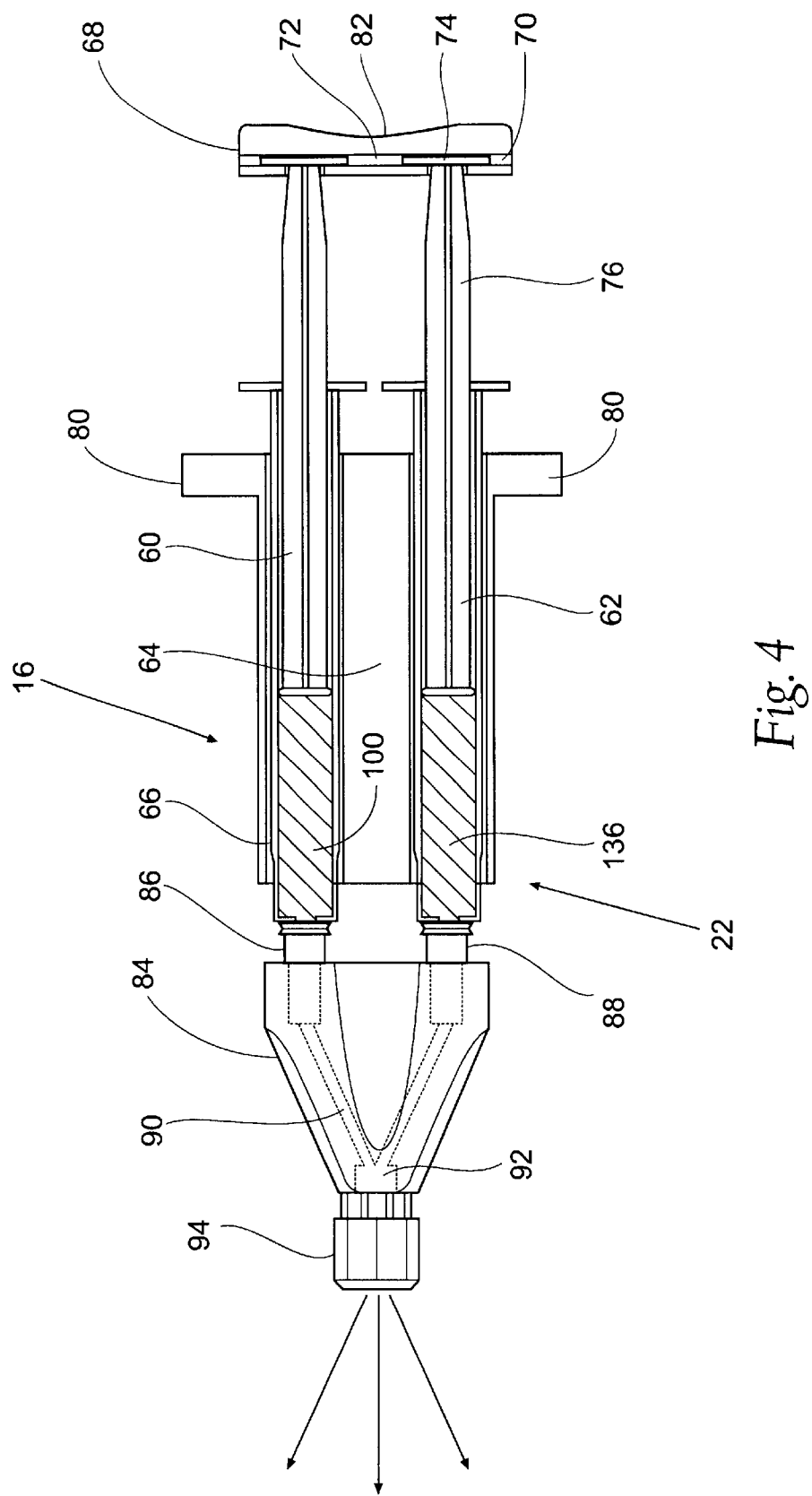
FIG. 4 is a side view of an introducer/mixer, with the syringes containing a liquid albumin solution and a liquid PEG solution mounted and ready for use, the introducer mixer having an attached mixing spray head to disperse the solutions to form the covering structure shown in FIGS. 2 and 3.

As FIG. 4 shows, the dispersing assembly 16 comprises a material introducer/mixer 22. The material introducer/mixer 22 receives the two dispensing syringes 60 and 62. The material introducer/mixer 22 allows the physician to uniformly dispense the two components in a liquid state from the dispensing syringes 60 and 62.

The material introducer/mixer 22 also mixes the components while flowing in the liquid state from the dispensing syringes 60 and 62.

To accomplish these functions (see FIG. 4), the material introducer/mixer 22 includes syringe support 64. The support 64 includes side-by-side channels 66 (see FIG. 1, too). The channel 66 accommodates in a snap-friction-fit the barrels of the syringes 60 and 62.

The material introducer/mixer 22 also includes a syringe clip 68. The syringe clip 68 includes spaced apart walls 70 forming an interior race 72. The race 72 receives in a sliding friction fit the thumb rests 74 of the pistons 76 of the dispensing syringes 60 and 62, in axial alignment with the syringe barrels carried by the syringe support 64. The syringe clip 68 mechanically links the syringe pistons 76 together for common advancement inside their respective syringe barrels.

To facilitate handling, the syringe support 64 includes opposed finger rests 80, and the syringe clip 68 includes a thumb rest 82. The orientation of these rests 80 and 82 parallel the orientation of the finger rests and thumb rests of a single syringe. The physician is thereby able to hold and operate multiple syringes 60 and 62 in the same way as a single syringe.

The material introducer/mixer 22 also includes a joiner 84. The joiner 84 includes side by side female luer fittings 86. The female luer fittings 86 each receives the threaded male luer fitting 88 at the dispensing end of the dispensing syringes 60 and 62. The female luer fittings 86 are axially aligned with the barrels 78 of the dispensing syringes 60 and 62 carried in the syringe support 64.

The physician is thereby able to quickly and conveniently ready the dispensing syringes 60 and 62 for use by securing the dispensing syringes to the joiner 84, snap fitting the syringe barrels 78 into the syringe support 64, and slide fitting the syringe thumb rests 74 into the clip 68.

The joiner 84 includes interior channels 90 coupled to the female luer fittings 86. The channels 90 merge at a Y-junction into a single outlet port 92. The joiner 84 maintains two fluids dispensed by the syringes 60 and 62 separately until they leave the joiner 84. This design minimizes plugging of the joiner 84 due to a mixing reaction between the two fluids. The syringe clip 68 ensures even application of individual solutions through the joiner 84.

The material introducer/mixer 22 further includes a mixing spray head 94, which, in use, is coupled to the single outlet port 92. In FIG. 1, the kit 14 contains several interchangeable mixing spray heads 94, in case one mixing spray head 94 becomes clogged during use.

The mixing spray head 94 may be variously constructed. It may, for example, comprise a spray head manufactured and sold by Hemaedics.

Figure 5:
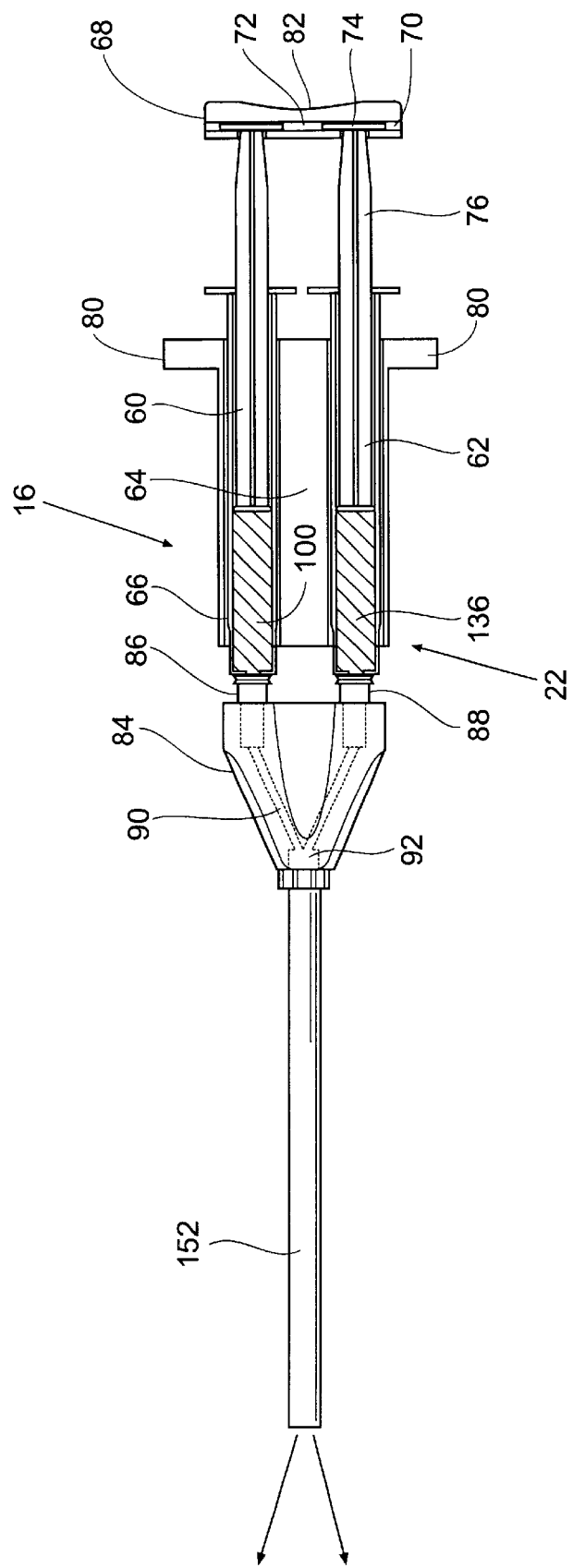
FIG. 5 is a side view of an introducer/mixer, with the syringes containing a liquid albumin solution and a liquid PEG solution mounted and ready for use, the introducer mixer having an attached cannula to disperse the solutions to form the covering structure shown in FIGS. 2 and 3.

Alternatively, the material introducer/mixer 22 can include a cannula 152, which, in use, can be coupled to the outlet port 92 instead of the mixing spray head (see FIG. 5).

Expressed in tandem from the dispensing syringes 60 and 62, which are mechanically linked together by the joiner 84, support 64, and clip 68, the two components of the barrier material come into contact in the liquid state either in the mixing spray head 94 or the cannula 152. Atomization of the two components occurs as they are dispersed through the mixing spray head 94 under pressure from operation of the mechanically linked dispensing syringes 60 and 62. Passage of the liquid components through the cannula 152 will channel-mix the materials. Either by atomization or channel mixing, the liquid components are sufficiently mixed to immediately initiate the cross-linking reaction.

The parts of the introducer/mixer 22 are made, e.g., by molding medical grade plastic materials, such as polycarbonate and acrylic.

III. The Kits

Figure 6A:
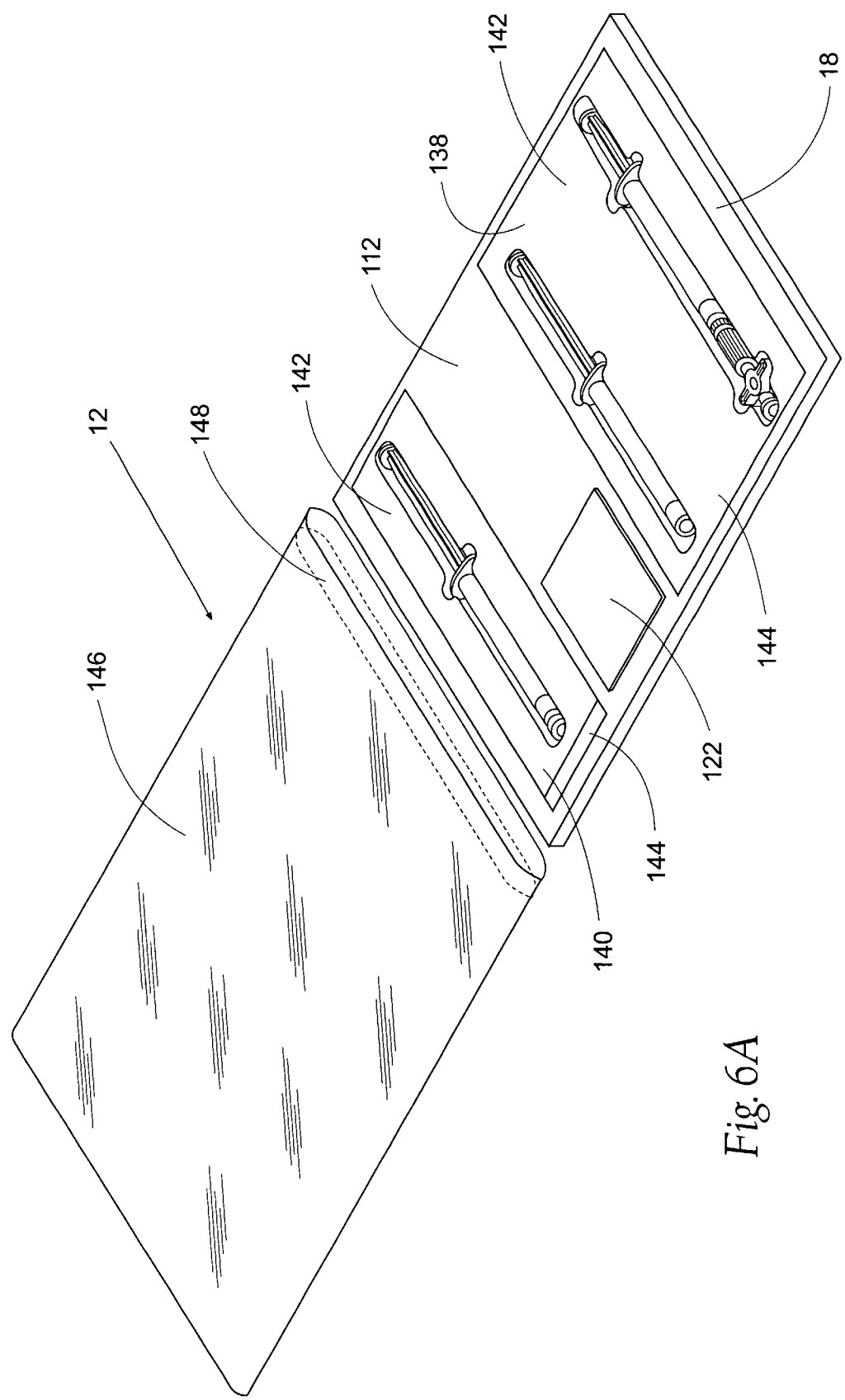
FIG. 6A is an exploded, perspective view of the kit shown in FIG. 1 that contains the liquid and solid components and syringe dispensers for the covering structure.
Figure 6B:
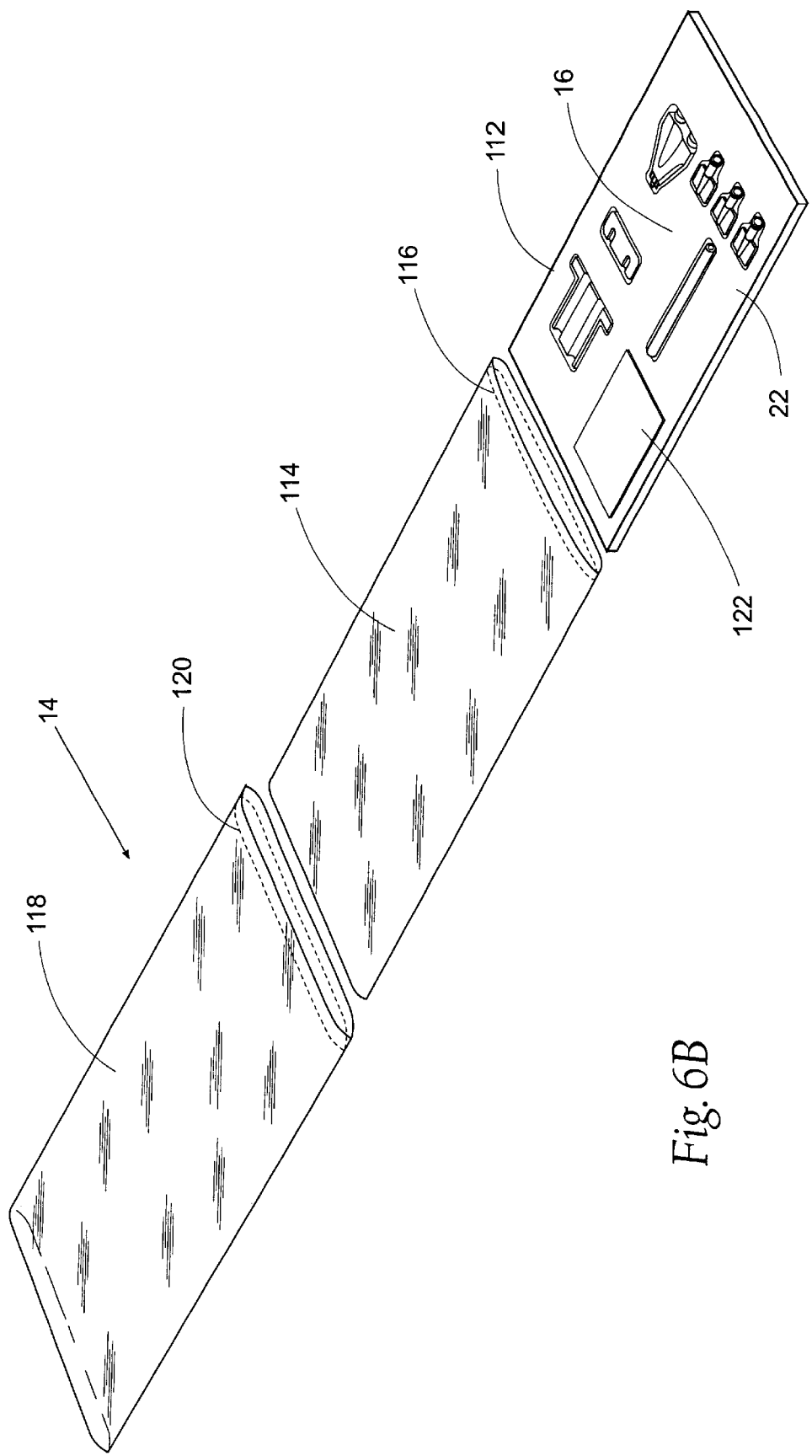
FIG. 6B is an exploded, perspective view of the kit shown in FIG. 1 that contains the introducer/mixer shown in FIGS. 4 and 5, which receives the syringes shown in FIG. 6A during use.

As FIGS. 6A and 6B show, in the illustrated embodiment, each kit 12 and 14 includes an interior tray 112 made, e.g., from die cut cardboard, plastic sheet, or thermo-formed plastic material.

The component assembly 18 is carried by the tray 112 in the kit 12 (see FIG. 6A). The dispersing assembly 16 is carried by the tray 112 in the kit 14 (see FIG. 6B).

As shown in FIG. 6B, the kit 14 includes an inner wrap 114, which is peripherally sealed by heat or the like, to enclose the tray 112 from contact with the outside environment. One end of the inner wrap 114 includes a conventional peel away seal 116. The seal 116 provides quick access to the tray 112 at the instant of use, which preferably occurs in a suitable sterile environment.

The kit 14 is further wrapped in an outer wrap 118, which is also peripherally sealed by heat or the like, to enclose the interior tray 112. One end of the inner wrap 118 includes a conventional peel away seal 120, to provide quick access to the interior tray 112 and its contents.

The outer wrap 118 and the inner wrap 114 are made, at least in part, from a material that is permeable to ethylene oxide sterilization gas, e.g., TYVEK™ plastic material (available from DuPont). Kit 12 is sterilized utilizing ethylene oxide gas or electron beam irradiation.

As shown in FIG. 6A, kit 12 includes a polymer package 138 (which contains the prefilled powder polymer syringe 62 and water syringe 104) and an albumin package 140 (which contains the prefilled albumin syringe 64). Each polymer package 138 and albumin package 140 includes an individual wrap 142, which is peripherally sealed by heat or the like, to enclose package 138 and 140 from contact with the outside environment. One end of the individual wrap 142 includes a conventional peel away seal 144, to provide quick access to the contents of the packages 138 and 140 at the instant of use.

Polymer package 138 and albumin package 140 are further wrapped in an outer wrap 118, which is also peripherally sealed by heat or the like. One end of the outer wrap 118 includes a conventional peel away seal 148, to provide quick access to the packages 138 and 140. After sterilization treatment, the packages 138 and 140 and the tray 112 are further wrapped in container 146 for the user's convenience.

The wraps 142 and 118 are made, at least in part, from a material that is permeable to ethylene oxide sterilization gas, e.g., TYVEK™ plastic material (available from DuPont). The albumin package 140 is prepared, sterilized utilizing ethylene oxide gas, and placed into kit 14. The polymer package 138 is prepared, sterilized utilizing electron beam irradiation, and place into kit 14.

In the illustrated embodiment, each kit 12 and 14 also preferably includes directions 122 for using the contents of the kit to carry out a desired procedure. The directions 122 can, of course vary, according to the particularities of the desired procedure. Furthermore, the directions 122 need not be physically present in the kits 12 and 14. The directions 122 can be embodied in separate instruction manuals, or in video or audio tapes.

IV. Using the System

A. Controlling or Arresting Diffuse Organ Bleeding

Figure 7A:
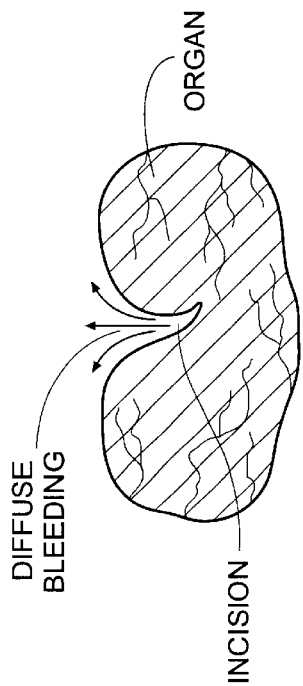
FIGS. 7A, 7B, and 7C illustrate use of the system shown in FIG. 1 to control or arrest diffuse organ bleeding.

In this embodiment, exemplary directions 122 are described, which instruct the physician how to use of the system 10 to arrest diffuse bleeding of an injured or compromised body organ. In the illustrated embodiment (see FIG. 7A), diffuse bleeding is shown to occur diagrammatically through an incision in the organ.

The system 10 is applicable for use to control or arrest diffuse bleeding in diverse types of organs, e.g., the liver, spleen, kidney, or bone. The cause of diffuse bleeding that the system 10 controls or arrests can also vary. The diffuse bleeding can occur as a result of trauma or accidental injury. The diffuse bleeding can also occur during normal surgical intervention, e.g., by organ resection, or tumor excision, or (in the case of bone) by sternotomy, orthopedic procedure, or craniotomy. The diffuse bleeding can also occur through needle tracks formed during tissue biopsy, or by capillary bed bleeding, as a result of saphenous vein harvesting, adhesiolysis, or tumor removal. It should be appreciated that the effectiveness of the system 10 does not depend upon where the diffuse bleeding is occurring or its underlying cause.

When use of the system 10 is desired, the outer wrap 118 of the kits 12 and 14 are removed. The trays 112, still contained in the inner wraps 118, are placed in the sterile operating field. The physician opens the inner wrap 118 of the kit 12 to gain access the first, second, and third syringes 60, 62, and 104.

The directions 122 for use instruct the physician to remove from the kit tray 112 the second dispensing syringe 62, which contains, in sterile powder form, a predetermined amount of the polymer 102 (e.g., about 0.3 to 0.5 g). The directions 122 also instruct the physician to remove from the kit 12 the third syringe 104, which contains sterile water 106 (e.g., about 2 cc). Both are contained in the polymer package 138.

As FIG. 10A shows, the directions 122 instruct the physician to couple the dispensing end of the water syringe 104 to the stopcock valve 108 on the second dispensing syringe 62. The stopcock valve 108 is closed at this point. As instructed by the directions 122, the physician opens the stopcock valve 108 (see FIG. 10B) and transfers water from the water syringe 104 into the powder 100 in the second dispensing syringe 62 (see FIG. 10C). The physician is instructed to repeatedly transfer the water and powder mixture between the two syringes 62 and 104, to syringe-mix the powder and water until all solids are dissolved. The syringe-mixing places the water soluble, polymer material into solution. The syringe-mixing process generally takes about two minutes.

After syringe mixing, the physician, following the directions 122, transfers the PEG solution 136 (about 2 cc) into one of the syringes (which, in the illustrated embodiment, is the second syringe 62). The physician waits for bubbles to dissipate, which generally takes about an additional two minutes.

According to the directions 122, the physician now closes the stopcock valve 108 (as FIG. 10D shows). The physician removes the stopcock valve 108 by unscrewing it from the luer fitting on the dispensing end of the second syringe 62. The PEG solution 136 is ready for use. Mixing of the PEG solution 136 should take place generally within one hour of use. If the PEG solution 136 remains unused over two hours after mixing, it should be discarded.

The directions 122 instruct the physician to remove from the second kit tray 112 the dispensing syringe 60 containing the albumin 100. As before described, the albumin 100 has been premixed in a buffered form to the desired concentration (e.g., 25%), then sterile filtered, and aseptically filled into the syringe 60. A closure cap normally closes the dispensing end inside the tray 112.

The physician now, or at a previous time, opens the outer wrap 118 of the kit 14 to gain access to the material introducer/mixer 22. The directions 122 instruct the physician to remove the closure cap and screw the dispensing end of the first syringe 60 to the luer fitting 86 on the joiner 84. The physician is also instructed to screw the dispensing end of the second syringe 62 (now containing the mixed PEG solution 136) to the other luer fitting 86 on the joiner 84.

Following the directions 122, the physician snaps the barrels 78 of the syringes 60 and 62 to the holder channels 66. The physician captures the thumb rests 74 of the two syringes 60 and 62 inside the race 72 of the syringe clip 68. The directions 122 instruct the physician to attach the joiner 84 to the mixing spray head 94.

Figure 7C:
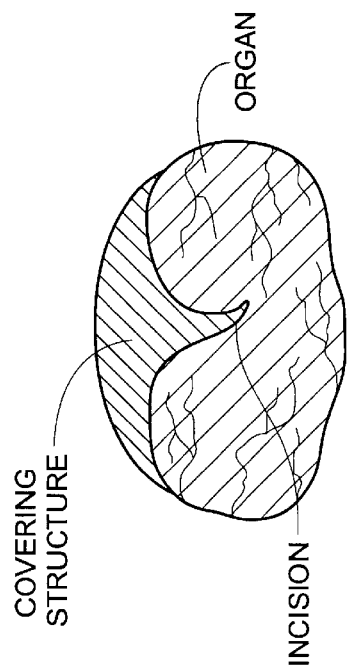
Figure 7B:
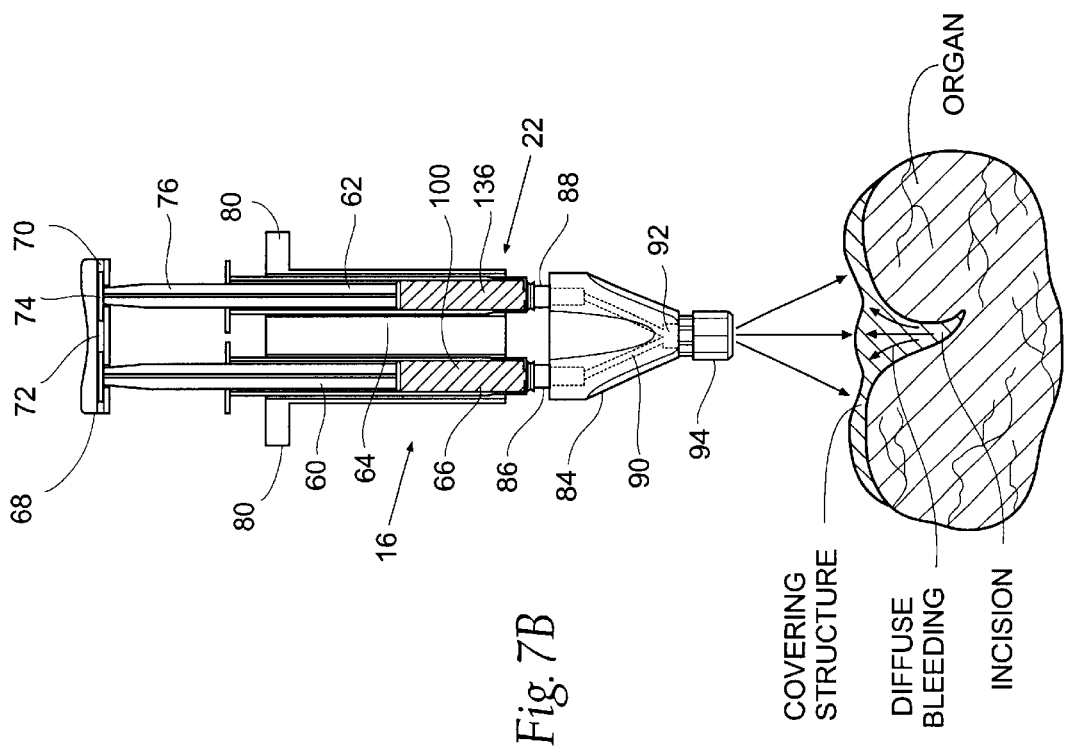

As FIG. 7B shows, the physician is instructed to position the mixing spray head 94 in a close relationship with the exposed site of diffuse bleeding on the organ. The physician applies manual pressure to the dispensing syringes 60 and 62. Albumin 100 from the first dispensing syringe 60 contacts the PEG solution 136 from the second dispensing syringe 62 in the mixing spray head 94. Atomization of the liquid components occurs through the mixing spray head 94 under pressure from operation of the mechanically linked dispensing syringes 60 and 62. The mixed liquids initiate the cross-linking reaction as they are dispersed onto the organ surface. Within seconds (as determined by the gel time), the liquid material transforms by in situ cross-linking into a non-liquid structure covering the diffuse bleeding site. As FIG. 7C shows, the covering structure adheres and conforms to the organ surface, including entry into any incision, blunt penetration, or other surface irregularity from which the diffuse bleeding emanates. Due to speed of cross-linking and the physical properties of the covering structure, diffuse bleeding does not wash away or dilute the liquid material as it transforms into the covering structure.

As cross linking rapidly occurs at the surface of the organ, the covering structure entraps diffused blood. Diffuse bleeding just as rapidly stops as the structure forms in situ, without need of any hemostatic agent. The covering structure forms an in situ barrier against further bleeding on the surface of the organ. The covering structure exists long enough to prevent further blood or fluid leakage while the compromised organ heals by natural processes.

EXAMPLE 3

Control of Bleeding from a Kidney Incision

A solution of 4-arm PEG succinimidyl glutarate, MW 10,000 (Shearwater Polymers, Huntsville, Ala.) was prepared by dissolving 0.40 g in 2.0 mL of water for injection. The albumin solution consisted of 25% human serum albumin, USP (Plasbumin-25, Bayer Corporation), buffered with 195 mM sodium carbonate and 120 mM sodium bicarbonate. Syringes containing 2.0 mL of the polymer solution and 2.0 mL of the albumin solution were connected to a joiner and sprayhead (DuoFlow, Hemaedics, Brentwood, Calif.).

The kidney of a sedated pig was exposed. An incision approximately an inch long and a quarter inch deep was made on the surface of the kidney. The continual flow of blood was temporarily collected with gauze. The gauze was then removed and the sprayable hemostatic solution, consisting of the polymer and albumin syringes, was applied using digital pressure.

As the two solutions were mixed in the sprayhead, the crosslinking reaction began. As the atomized, mixed fluid landed on the surface of the bleeding kidney, the gelation of the solution occurred. The hydrogel adhered tenaciously to the surface of the kidney, preventing blood from flowing. The hydrogel also had sufficient cohesive strength to prevent rupture. Without the use of a hemostatic agent, hemostasis occurred instantaneously using the mechanical barrier of the hydrogel.

EXAMPLE 4

Control of Bleeding from a Spleen Incision

A solution of 4-arm PEG succinimidyl glutarate, MW 10,000 (Shearwater Polymers, Huntsville, Ala.) was prepared by dissolving 0.40 g in 2.0 mL of water for injection. The albumin solution consisted of 25% human serum albumin, USP (Plasbumin-25, Bayer Corporation), buffered with 195 mM sodium carbonate and 120 mM sodium bicarbonate. Syringes containing 2.0 mL of the polymer solution and 2.0 mL of the albumin solution were connected to a joiner and sprayhead (DuoPlow, Hemaedics, Brentwood, Calif.).

The spleen of a sedated pig was exposed. An incision approximately an inch long and a quarter inch deep was made on the surface of the spleen. The continual flow of blood was temporarily collected with gauze. The gauze was then removed and the sprayable hemostatic solution, consisting of the polymer and albumin syringes, was applied using digital pressure.

As the two solutions were mixed in the sprayhead, the crosslinking reaction began. As the atomized, mixed fluid landed on the surface of the bleeding spleen, the gelation of the solution occurred. The hydrogel adhered tenaciously to the surface of the spleen, preventing blood from flowing. The hydrogel also had sufficient cohesive strength to prevent rupture. Without the use of a hemostatic agent, hemostasis occurred instantaneously using the mechanical barrier of the hydrogel.

EXAMPLE 5

Control of Bleeding from a Liver Incision

A solution of 4-arm PEG succinimidyl glutarate, MW 10,000 (Shearwater Polymers, Huntsville, Ala.) was prepared by dissolving 0.40 g in 2.0 mL of water for injection. The albumin solution consisted of 25% human serum albumin, USP (Plasbumin-25, Bayer Corporation), buffered with 195 mM sodium carbonate and 120 mM sodium bicarbonate. Syringes containing 2.0 mL of the polymer solution and 2.0 mL of the albumin solution were connected to a joiner and sprayhead (DuoFlow, Hemaedics, Brentwood, Calif.).

The liver of a sedated pig was exposed. An incision approximately an inch long and a quarter inch deep was made on the surface of the liver. The continual flow of blood was temporarily collected with gauze. The gauze was then removed and the sprayable hemostatic solution, consisting of the polymer and albumin syringes, was applied, using digital pressure.

As the two solutions were mixed in the sprayhead, the crosslinking reaction began. As the atomized, mixed fluid landed on the surface of the bleeding liver, the gelation of the solution occurred. The hydrogel adhered tenaciously to the surface of the liver, preventing blood from flowing. The hydrogel also had sufficient cohesive strength to prevent rupture. Without the use of a hemostatic agent, hemostasis occurred instantaneously using the mechanical barrier of the hydrogel.

B. Controlling or Arresting Air Leaks From a Lung Incision

Figure 8A:
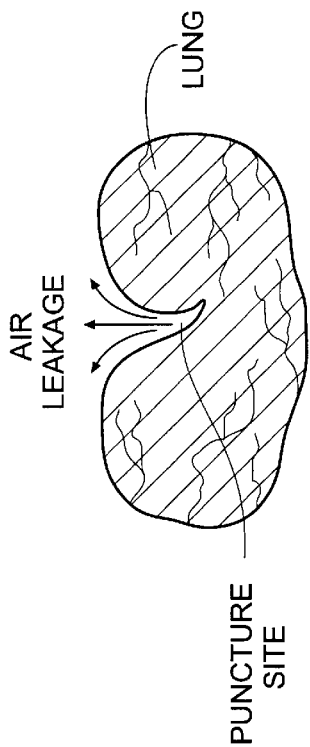
FIGS. 8A, 8B, and 8C demonstrate use of the system shown in FIG. 1 to seal a puncture site in a lung.

The exemplary directions 122 just described can be modified to instruct the physician how to use of the system 10 to control or arrest the leakage of air through a perforation or puncture in the lung caused, e.g., by trauma (see FIG. 8A).

In this embodiment, the instructions 122 instruct the physician to prepare the dispensing syringes 60 and 62 and coupled them to the joiner 84 in the manner previously set forth. The physician is instructed to attach the mixing spray head 84 and position the mixing spray head 94 in a close relationship with lung puncture site. The lung is deflated (see FIG. 8B).

Figure 8C:
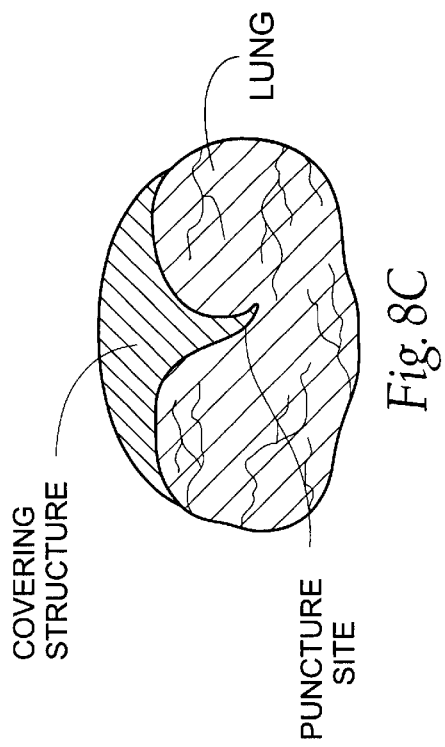
Figure 8B:
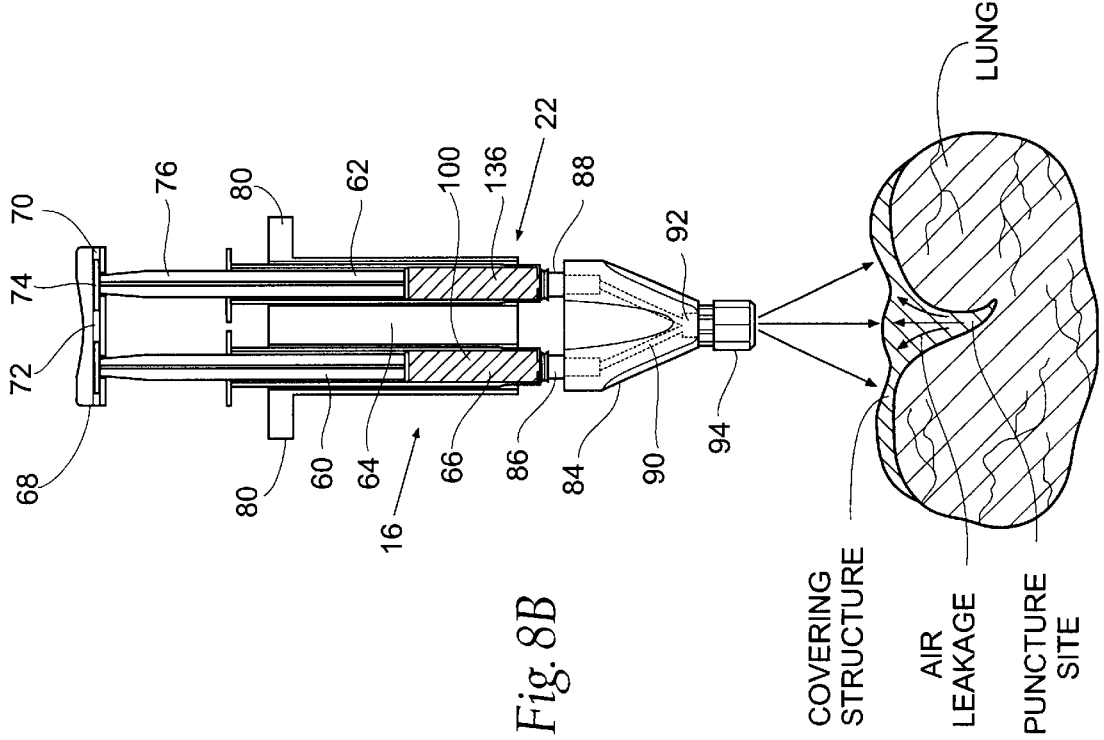

In the manner previously described, the physician applies manual pressure to the dispensing syringes 60 and 62 (as FIG. 8B shows). Albumin 100 from the first dispensing syringe 60 contacts the PEG solution 136 from the second dispensing syringe 62 in the mixing spray head 94. Atomization of the liquid components also occurs through the mixing spray head 94 under pressure from operation of the mechanically linked dispensing syringes 60 and 62. The mixed liquids initiate the cross-linking reaction as they are dispersed into contact with tissue surrounding the lung puncture site. Within seconds, the liquid material transforms by in situ cross-linking into a non-liquid structure covering the puncture site (see FIG. 8C). Air leaks through the puncture site stop as the structure forms in situ. The covering structure exists long enough to prevent further air leaks, while the lung tissue heals by natural processes.

EXAMPLE 5

Control of Air Leaks from a Lung Incision

A solution of 4-arm PEG succinimidyl glutarate, MW 10,000 (Shearwater Polymers, Huntsville, Ala.) was prepared by dissolving 0.40 g in 2.0 mL of water for injection. The albumin solution consisted of 25% human serum albumin, USP (Plasbumin-25, Bayer Corporation), buffered with 195 mM sodium carbonate and 120 mM sodium bicarbonate. Syringes containing 2.0 mL of the polymer solution and 2.0 mL of the albumin solution were connected to a joiner and sprayhead (DuoFlow, Hemaedics, Brentwood, Calif.).

The lung of a euthanized, intubated pig was exposed. An incision approximately an inch long and a quarter inch deep was made on the surface of the lung. An air leak was confirmed by manually inflated the lung and listening for the hissing sound of air leaks. The lung was deflated and the surgical sealant, consisting of the polymer and albumin syringes, was applied using digital pressure.

As the two solutions were mixed in the sprayhead, the crosslinking reaction began. As the atomized, mixed fluid landed on the surface of the lung, the gelation of the solution occurred. The hydrogel was firmly adherent to the surface of the lung. After about 10 seconds, the lungs were manually inflated and examined for the presence of air leaks. The hydrogel remained firmly attached to the lung tissue, even during and after the expansion of the lungs. Air leaks were not present after the application of the hydrogel surgical sealant. The hydrogel showed sufficient adhesion, cohesion, and elasticity to seal air leaks of lung tissue.

C. Sealing Anastomosis

Figure 9A:
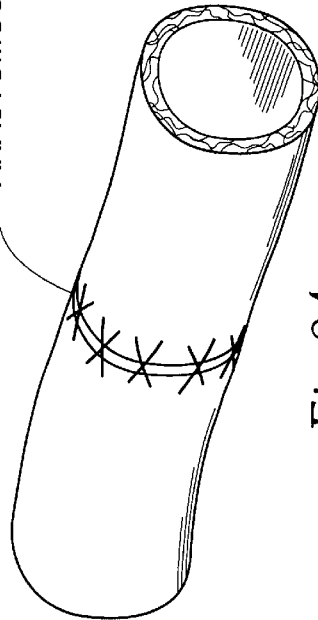
FIGS. 9A, 9B, and 9C illustrate use of the system shown in FIG. 1 to control or arrest bleeding through an anastomosis.

The exemplary directions 122 just described can be modified to instruct the physician how to use of the system 10 as a surgical sealant along suture lines or about surgical staples, forming an anastomosis (see FIG. 9A). The sutures or staples can be used, e.g., to join blood vessels, bowels, ureter, or bladder. The sutures or staples can also be used in the course of neurosurgery or ear-nose-throat surgery.

Figure 9C:
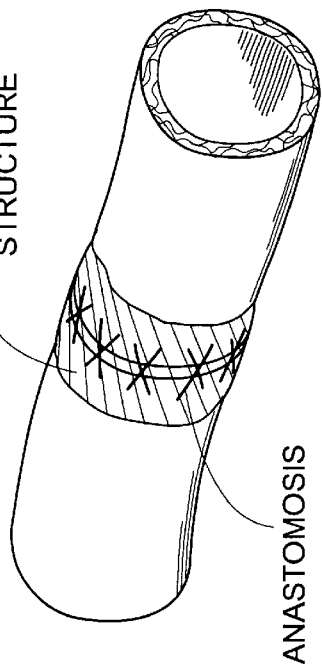
Figure 9B:
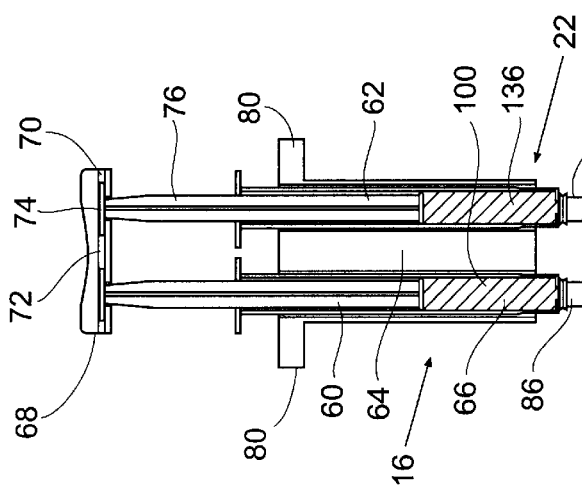
Figure 9B:
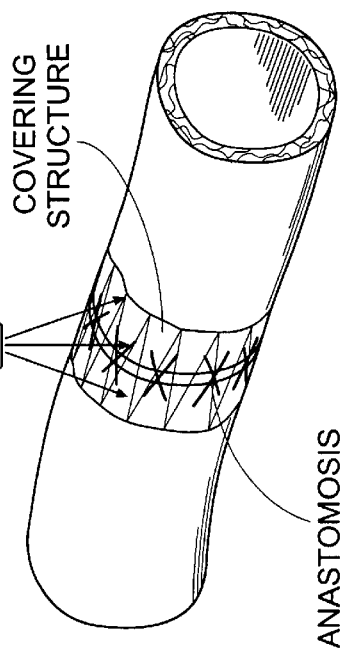

In this embodiment, the instructions 122 instruct the physician to prepare the dispensing syringes 60 and 62 and coupled them to the joiner 84 in the manner previously set forth. The physician is instructed to attach the mixing spray head 84 and position the mixing spray head 94 in a close relationship with the anastomosis (as FIG. 9B shows).

In the manner previously described, the physician applies manual pressure to the dispensing syringes 60 and 62. Albumin 100 from the first dispensing syringe 60 contacts the PEG solution 136 from the second dispensing syringe 62 in the mixing spray head 94. Atomization of the liquid components also occurs through the mixing spray head 94 under pressure from operation of the mechanically linked dispensing syringes 60 and 62. The mixed liquids initiate the cross-linking reaction as they are dispersed into contact with tissue along the anastomosis (see FIG. 9B). Within seconds, the liquid material transforms by in situ cross-linking into a non-liquid structure covering the anastomosis (see FIG. 9C). Blood or fluid seepage through the anastomosis stop as the structure forms in situ. The covering structure exists long enough to prevent further blood or fluid leaks, while tissue along the anastomsis heals by natural processes.

It should be appreciated that the compositions, systems, and methods described are applicable for use to control or arrest bleeding or fluid leaks in tissue throughout the body, including by way of example, the following surgical sites and indications:

(i) In general surgery, such as in the liver (resection, tumor excision or trauma); in the spleen (trauma or iatrogenic capsular avlsion; oncology in general (excision of tumors); or laporoscopic cholecystectomy (Lapchole) (to control bleeding from the gall bladder bed);

(ii) In vascular surgery, such as peripheral vascular procedures; anastomosis sites (carotid, femoral and popliteal arteries); or aneurysms;

(iii) In the head, such as craniotomy (to control bone bleeding from cut bone edges or bleeding from soft tissue); or superior sagittal sinus (to control bleeding from damage to thin wall sinus and access to sinus);

(iv) To treat arteriovenous malformation (AVM) (to control blood vessel bleeding from smaller vessels);

(v) To treat tumor complications, such as tumor bed bleeding or damage to soft tissue due to excisions;

(vi) To treat hematomas, such as in the control of bleeding in soft tissues and adjacent to vessels;

(vii) In orthopedic applications, such as laminectomy or discectomy, to control bone bleeding from the vertebrae; or spinal reconstruction and fusion, to control epidural vessels and vertabral bleeders; or in hip and knee replacements, to control of bleeding in smooth muscle tissue, soft tissue;

(viii) In cardiovascular and thoracic surgery, such as control of anastomosis sites in coronary artery bypass graft (C.A.B.G.); aorta reconstruction and repair, to control bleeding in surrounding tissue; or chest cavity access through the sternum, to control bone bleeding or soft tissue bleeding;

(ix) In urology, such as retropubic prostatectomy, to control bleeding in soft tissue; or partial nephrectomy, to control parenchymal bleeding; in bladder substitution, uretero-intestinal anastomosis; urethral surgery; open urethral surgery; or vasovasostomy;

(x) In ear-neck-throat surgery, such as during clearing of the frontal, thmoid, sphenoid and maxillary sinuses; or in polyp removal;

(xi) In plastic and reconstructive surgery, such as face lifts, rhinoplasty, blepharplasty, or breast surgery;

(xii) In emergency procedures involving trauma, tissue fracture, or abrasions.

The features of the invention are set forth in the following claims.

We claim:

1. A biocompatible and biodegradable material applied to arrest the flow of blood or to seal tissue comprising a mixture of a protein solution comprising recombinant or natural human serum albumin at a concentration of about 25% or less and a polymer solution including a derivative of a hydrophilic polymer with a functionality of at least three, wherein, upon mixing, the protein solution and the polymer solution cross-link to form a mechanical non-liquid covering structure without of a photo-intiator and ultraviolet light energy.

2. A material according to claim 1, wherein the protein solution includes a buffer.

3. A material according to claim 2, wherein the buffer includes carbonate or phosphate.

4. A material according to claim 2, wherein the buffer has a concentration of about 0.3 M to about 0.4 M.

5. A material according to claim 4, wherein the buffer comprises carbonate at a concentration of about 0.3 M and a pH value of about 8 to about 10.

6. A material according to claim 1, wherein the protein solution has a pH value of between about 7 to about 10.

7. A material according to claim 6, wherein the pH value is about 8 to about 10.

8. A material according to claim 1, wherein the polymer is electrophilically derivatized.

9. A material according to claim 1, wherein the polymer solution includes a derivative of a polymer selected from a group consisting essentially of poly(ethylene glycol), poly(ethylene oxide), poly(vinyl alcohol), poly(vinylpyrrolidone), poly(ethyloxazoline), poly(ethylene glycol)-co-poly(propylene glycol) block copolymers, or electrophilically derivatized polysaccharides, carbohydrates, or proteins.

10. A material according to claim 1, wherein the polymer is comprised of poly(ethylene glycol) (PEG).

11. A material according to claim 10, wherein the PEG has a molecular weight of between about 1,000 and about 30,000 g/mole.

12. A material according to claim 11, wherein the PEG has a molecular weight of between about 2,000 and about 15,000 g/mole.

13. A material according to claim 11, wherein the PEG has a molecular weight of between about 10,000 and 15,000 g/mole.

14. A material according to claim 10, wherein the PEG comprises a multi-armed polymer structure.

15. A material according to claim 1, wherein the polymer comprises a compound of the formula PEG-(DCR-CG)$_n$, where PEG is poly(ethylene glycol), DCR is a degradation control region, CG is a cross-linking group, and n is equal to or greater than three.

16. A material according to claim 15, wherein the compound comprises a multi-armed polymer structure.

17. A material according to claim 15, wherein the degradation control region (DCR) comprises a hydrolytically degradable moiety.

18. A material according to claim 17, wherein the hydrolytically degradable moiety includes saturated di-acids, unsaturated di-acids, poly(glycolic acid), poly(DL-lactic acid), poly(L-lactic acid), poly(ε-caprolactone), poly(δ-valerolactone), poly(γ-butyrolactone), poly(amino acids), poly(anhydrides), poly(orthoesters), poly(orthocarbonates), or poly(phosphoesters).

19. A material according to claim 15, wherein the degradation control region (DCR) comprises an enzymatically degradable region.

20. A material according to claim 19, wherein the enzymatically degradable region includes Leu-Glyc-Pro-Ala (collagenes sensitive linkage) or Gly-Pro-Lys (plasmin sensitive linkage).

21. A material according to claim 15, wherein the degradable control region (DGR) includes ester containing linkages.

22. A material according to claim 21, wherein the degradable control region (GCR) includes succinic acid or glutaric acid.

23. A material according to claim 15, wherein the cross-linking group (CG) includes an active ester.

24. A material according to claim 23, wherein the active ester includes an ester of N-hydroxysuccinimide.

25. A material according to claim 15, wherein the cross-linking group (CG) selectively reacts with sulfhydryl groups.

26. A material according to claim 25, wherein the cross-linking group (CG) includes vinyl sulfone, N-ethyl maleimide, iodoacetamide, or orthopyridyl disulfide.

27. A material according to claim 15, wherein the cross-linking group (CG) selectively reacts with amino groups.

28. A material according to claim 27, wherein the cross-linking group (CG) includes aldehydes.

29. A material according to claim 15, wherein the cross-linking group (CG) reacts with sulfhydryl, primary amino, and secondary amino groups.

30. A material according to claim 15, wherein the cross-linking group (CG) include active esters, epoxides, carbonylimidazole, nitrophenyl carbonates, tresylate, mesylate, tosylate, or isocyanate.

31. A material according to claim 15, wherein the cross-linking group (CG) is present in a concentration of less than about 5% of total mass of the compound.

32. A material according to claim 15, wherein the cross-linking group (CG) is present in a concentration of about 1% or less of total mass of the compound.

33. A material according to claim 15, wherein the PEG comprises a 4-arm PEG, the degradation control region comprises glutaric acid, and the cross-linking group includes a N-hydroxysuccinimide ester.

34. A material according to claim 31, wherein the 4-arm PEG has a molecular weight of about 10,000 g/mole.

35. A material according to claim 15, wherein the compound comprises poly(ethylene glycol) tetra-succinimidyl glutarate.

36. A material according to claim 15, wherein the compound comprises poly(ethylene glycol)tetra-succinimidyl succinate.

37. A material according to claim 1, wherein the polymer solution includes poly(ethylene glycol)tetra-succinimidyl glutarate.

38. A material according to claim 37, wherein the polymer solution includes water.

39. A material according to claim 1, wherein the polymer has a functionality of four.

40. A material according to claim 1, wherein the polymer solution includes poly(ethylene glycol)tetra-succinimidyl succinate.

41. A material according to claim 1, wherein the polymer solution has a concentration that ranged from about 5% to about 35% w/w.

42. A biocompatible and biodegradable material applied to arrest the flow of blood or to seal tissue comprising a mixture of a protein solution including a buffer having a concentration of about 0.3 M to 0.4 M, and a polymer solution including a derivative of a hydrophilic polymer with a functionality of at least three, wherein, upon mixing, the protein solution and the polymer solution cross-link to form a mechanical non-liquid covering structure.

43. A material according to claim 42, wherein the buffer comprises carbonate at a concentration of about 0.3 M and a pH value of about 8 to about 10.

44. A biocompatible and biodegradable material applied to arrest the flow of blood or to seal tissue comprising a mixture of a protein solution and a polymer solution including a derivative of a hydrophilic polymer with a functionality of at least three, the polymer comprising a compound of the formula PEG-(DCR-CG)n, where PEG is poly (ethylene glycol), DCR is a degradation control region, CG is a cross-linking group, and n is equal to or greater than three, wherein, upon mixing, the protein solution and the polymer solution cross-link to form a mechanical non-liquid covering structure.

45. A material according to claim 44, wherein the compound comprises a multi-armed polymer structure.

46. A material according to claim 44, wherein the degradation control region (DCR) comprises a hvdrolytically degradable moiety.

47. A material according to claim 46, wherein the hydrolytically degradable moiety includes saturated di-acids, unsaturated di-acids, poly(glycolic acid), poly(DL-lactic acid), poly(L-lactic acid), poly(-caprolactone), poly(-valerolactone), poly(-butyrolactone), poly(amino acids), poly(anhydrides), poly(orthoesters), poly(orthocarbonates), or poly(phosphoesters).

48. A material according to claim 44, wherein the degradation control region (DCR) comprises an enzymatically degradable region.

49. A material according to claim 48, wherein the enzymatically degradable region includes Leu-Clyc-Pro-Ala (collagenes sensitive linkage) or Gly-Pro-Lys (plasmin sensitive linkage).

50. A material according to claim 44, wherein the degradable control region (DGR) includes ester containing linkages.

51. A material according to claim 50, wherein the degradable control region (GCR) includes succinic acid or glutaric acid.

52. A material according to claim 44, wherein the cross-linking group (CG) includes an active ester.

53. A material according to claim 52, wherein the active ester includes an ester of N-hydroxysuccinimide.

54. A material according to claim 44, wherein the cross-linking group (CG) selectively reacts with sulfhydryl groups.

55. A material according to claim 54, wherein the cross-linking group (CG) includes vinyl sulfone, N-ethyl maleimide, iodoacetamide, or orthopyridyl disulfide.

56. A material according to claim 44, wherein the cross-linking group (CG) selectively reacts with amino groups.

57. A material according to claim 56, wherein the cross-linking group (CG) includes aldehydes.

58. A material according to claim 44, wherein the cross-linking group (CG) reacts with sulfhydryl, primary amino, and secondary amino groups.

59. A material according to claim 44, wherein the cross-linking group (CG) include active esters, epoxides, carbonylimidazole, nitrophenyl carbonates, tresylate, mesylate, tosylate, or isocyanate.

60. A material according to claim 44, wherein the cross-linking group (CG) is present in a concentration of less than about 5% of total mass of the compound.

61. A material according to claim 44, wherein the cross-linking group (CG) is present in a concentration of about 1% or less of total mass of the compound.

62. A material according to claim 44, wherein the PEG comprises a 4-arm PEG, the degradation control region comprises glutaric acid, and the cross-linking group includes a N-hydroxysuccinimide ester.

63. A material according to claim 60, wherein the 4-arm PEG has a molecular weight of about 10,000 g/mole.

64. A material according to claim 44, wherein the compound comprises poly(ethylene glycol) tetra-succinimidyl glutarate.

65. A material according to claim 44, wherein the compound comprises poly(ethylene giycol)tetra-succinimidyl succinate.

66. A material according to claim 44, wherein the polymer solution includes poly(ethylene glycol)tetra-succinimidyl glutarate.

67. A material according to claim 66, wherein the polymersolution includes water.

68. A material according to claim 44, wherein the polymer has a functionality of four.

69. A material according to claim 44, wherein the polymer solution includes poly(ethylene glycol)tetra-succinimidyl succinate.

70. A material according to claim 44, wherein the polymer solution has a concentration that ranged from about 5% to about 35% w/w.

71. A biocompatible and biodegradable material applied to arrest the flow of blood or to seal tissue comprising a mixture of a protein solution and a polymer solution including a derivative of a hydrophilic polymer with a functionality of four, wherein, upon mixing, the protein solution and the polymer solution cross-link to form a mechanical non-liquid covering structure.

72. A biocompatible and biodegradable material applied to arrest the flow of blood or to seal tissue comprising a mixture of a protein solution and a polymer solution including a derivative of a hydrophilic polymer with a functionality of at least three, the polymer solution including poly(ethylene glycol)tetra-succinimidyl succinate wherein, upon mixing, the protein solution and the polymer solution cross-link to form a mechanical non-liquid covering structure.

73. A material according to claim 42 or 44 or 71 or 72, wherein the protein solution includes recombinant or natural human serum albumin.

74. A material according to claim 42 or 44 or 71 or 72, wherein the protein solution comprises a hydrophilic protein selected from a group consisting essentially of albumin, gelatin, antibodies, serum fractions, or serum.

75. A material according to claim 42 or 44 or 71 or 72, wherein the protein solution comprises a water soluble derivative of a hydrophobic protein selected from a group consisting essentially of collagen, fibrinogen, elastin, chitosan, or hyaluronic acid.

* * * * *

UNITED STATES PATENT AND TRADEMARK OFFICE
CERTIFICATE OF CORRECTION

PATENT NO. : 6,458,147 B1
DATED : October 1, 2002
INVENTOR(S) : Cruise et al.

It is certified that error appears in the above-identified patent and that said Letters Patent is hereby corrected as shown below:

Title page,
Item [56], References Cited, OTHER PUBLICATIONS, should read:
-- West, JL et al., "Proteolytically Degradable Hydrogel", Apr. 30-May 4, 1997, 23rd Annual Meeting of the Society for Biomaterials, New Orleans, Louisiana. --

Column 15, line 36 through Column 20, line 9,
The claims of the issued patent should read as follows:

1. A biocompatible and biodegradable material applied to arrest the flow of blood or to seal tissue comprising a mixture of a protein solution comprising recombinant or natural human serum albumin at a concentration of about 25% or less and a polymer solution including a derivative of a hydrophilic polymer with a functionality of at least three, wherein, upon mixing, the protein solution and the polymer solution cross-link to form a mechanical non-liquid covering structure without use of a photo-initiator and ultraviolet light energy.
2. A material according to claim 1, wherein the protein solution includes a buffer.
3. A material according to claim 2, wherein the buffer includes carbonate or phosphate.
4. A material according to claim 2, wherein the buffer has a concentration of about 0.3 M to about 0.4 M.
5. A material according to claim 4, wherein the buffer comprises carbonate at a concentration of about 0.3 M and a pH value of about 8 to about 10.
6. A material according to claim 1, wherein the protein solution has a pH value of between about 7 to about 10.
7. A material according to claim 6, wherein the pH value is about 8 to about 10.
8. A material according to claim 1, wherein the polymer is electrophilically derivatized.
9. A material according to claim 1, wherein the polymer solution includes a derivative of a polymer selected from a group consisting essentially of poly(ethylene glycol), poly(ethylene oxide), poly(vinyl alcohol), poly(vinylpyrrolidone), poly(ethyloxazoline), poly(ethylene glycol)-co-poly(propylene glycol) block copolymers, or electrophilically derivatized polysaccharides, carbohydrates, or proteins.
10. A material according to claim 1, wherein the polymer is comprised of poly(ethylene glycol)(PEG).
11. A material according to claim 10, wherein the PEG has a molecular weight of between about 1,000 and about 30,000 g/mole.
12. A material according to claim 11, wherein the PEG has a molecular weight of between about 2,000 and about 15,000 g/mole.
13. A material according to claim 11, wherein the PEG has a molecular weight of between about 10,000 and 15,000 g/mole.
14. A material according to claim 10, wherein the PEG comprises a multi-armed polymer structure.
15. A material according to claim 1, wherein the polymer comprises a compound of the formula PEG-(DCR-CG)n, where PEG is poly(ethylene glycol), DCR is a degradation control region, CG is a cross-linking group, and n is equal to or greater than three.
16. A material according to claim 15, wherein the compound comprises a multi-armed polymer structure.
17. A material according to claim 15, wherein the degradation control region (DCR) comprises a hydrolytically degradable moiety.
18. A material according to claim 17, wherein the hydrolytically degradable moiety includes saturated di-acids, unsaturated di-acids, poly(glycolic acid), poly(DL-lactic acid), poly(L-lactic acid), poly( -caprolactone), poly( -valerolactone), poly( -butyrolactone), poly(amino acids), poly(anhydrides), poly(orthoesters), poly(orthocarbonates), or poly(phosphoesters).
19. A material according to claim 15, wherein the degradation control region (DCR) comprises an enzymatically degradable region.
20. A material according to claim 19, wherein the enzymatically degradable region includes Leu-Glyc-Pro-Ala (collagenes sensitive linkage) or Gly-Pro-Lys (plasmin sensitive linkage).
21. A material according to claim 15, wherein the degradable control region (DGR) includes ester containing linkages.
22. A material according to claim 21, wherein the degradable control region (GCR) includes succinic acid or glutaric acid.

UNITED STATES PATENT AND TRADEMARK OFFICE
CERTIFICATE OF CORRECTION

PATENT NO. : 6,458,147 B1
DATED : October 1, 2002
INVENTOR(S) : Cruise et al.

It is certified that error appears in the above-identified patent and that said Letters Patent is hereby corrected as shown below:

Claims, continued:

23. A material according to claim 15, wherein the cross-linking group (CG) includes an active ester.
24. A material according to claim 23, wherein the active ester includes an ester of N-hydroxysuccinimide.
25. A material according to claim 15, wherein the cross-linking group (CG) selectively reacts with sulfhydryl groups.
26. A material according to claim 25, wherein the cross-linking group (CG) includes vinyl sulfone, N-ethyl maleimide, iodoacetamide, or orthopyridyl disulfide.
27. A material according to claim 15, wherein the cross-linking group (CG) selectively reacts with amino groups.
28. A material according to claim 27, wherein the cross-linking group (CG) includes aldehydes.
29. A material according to claim 15, wherein the cross-linking group (CG) reacts with sulfhydryl, primary amino, and secondary amino groups.
30. A material according to claim 15, wherein the cross-linking group (CG) include active esters, epoxides, carbonylimidazole, nitrophenyl carbonates, tresylate, mesylate, tosylate, or isocyanate.
31. A material according to claim 15, wherein the cross-linking group (CG) is present in a concentration of less than about 5% of total mass of the compound.
32. A material according to claim 15, wherein the cross-linking group (CG) is present in a concentration of about 1% or less of total mass of the compound.
33. A material according to claim 15, wherein the PEG comprises a 4-arm PEG, the degradation control region comprises glutaric acid, and the cross-linking group includes a N-hydroxysuccinimide ester.
34. A material according to claim 31, wherein the 4-arm PEG has a molecular weight of about 10,000 g/mole.
35. A material according to claim 15, wherein the compound comprises poly(ethylene glycol) tetra-succinimidyl glutarate.
36. A material according to claim 15, wherein the compound comprises poly(ethylene glycol)tetra-succinimidyl succinate.
37. A material according to claim 1, wherein the polymer solution includes poly(ethylene glycol)tetra-succinimidyl glutarate.
38. A material according to claim 37, wherein the polymer solution includes water.
39. A material according to claim 1, wherein the polymer has a functionality of four.
40. A material according to claim 1, wherein the polymer solution includes poly(ethylene glycol)tetra-succinimidyl succinate.
41. A material according to claim 1, wherein the polymer solution has a concentration that ranged from about 5% to about 35% w/w.

Signed and Sealed this

Second Day of December, 2003

JAMES E. ROGAN
*Director of the United States Patent and Trademark Office*